United States Patent
Alleckson et al.

(10) Patent No.: US 6,336,900 B1
(45) Date of Patent: Jan. 8, 2002

(54) HOME HUB FOR REPORTING PATIENT HEALTH PARAMETERS

(75) Inventors: Todd D. Alleckson, Auburn; Energy Cruse, II, Foster City, both of CA (US); Karyn Grant, Sudbury, MA (US); Robert C. Leichner, Menlo Park, CA (US); Gaurang C. Mehta, Union City, CA (US); James M. Rueter, Mountain View, CA (US); Thomas A. Shoup, Los Altos, CA (US); Alexander L. Tudor, Mountain View, CA (US); Ronald T. Yamada, Belmont, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/290,155

(22) Filed: Apr. 12, 1999

(51) Int. Cl.⁷ .................................................. A61B 5/00
(52) U.S. Cl. ..................... 600/485; 128/904; 600/300
(58) Field of Search ................................. 600/300, 301, 600/481, 500, 544–545; 128/900, 903, 904; 705/2–3

(56) References Cited

U.S. PATENT DOCUMENTS

| | | | |
|---|---|---|---|
| 4,803,625 A | 2/1989 | Fu et al. ................. 364/413.02 |
| 5,142,484 A | 8/1992 | Kaufman et al. ........... 222/638 |
| 5,265,010 A | 11/1993 | Paganelli et al. | |
| 5,331,549 A | 7/1994 | Crawford, Jr. | |
| 5,357,427 A | 10/1994 | Langen | |
| 5,404,292 A | 4/1995 | Hendrickson | |
| 5,558,638 A | 9/1996 | Evers et al. | |
| 5,576,952 A | 11/1996 | Stutman et al. | |
| 5,619,991 A | * 4/1997 | Sloane ........................ 600/300 |
| 5,626,144 A | 5/1997 | Tacklind et al. | |
| 5,704,366 A | 1/1998 | Tacklind et al. | |
| 5,722,418 A | * 3/1998 | Bro .............................. 600/300 |
| 5,732,709 A | 3/1998 | Tacklind et al. | |
| 5,832,448 A | 11/1998 | Brown | |
| 5,857,967 A | 1/1999 | Frid et al. | |
| 6,093,146 A | * 7/2000 | Filangeri ..................... 600/300 |

* cited by examiner

*Primary Examiner*—Eric F. Winakur
*Assistant Examiner*—Michael Astorino (57) ABSTRACT

An apparatus for reporting a patient's health parameter to a remote data management center. The apparatus has measurement units and a home hub. A measurement unit includes a sensor for sensing measurements of a health parameter and a transmitter for transmitting wirelessly data derived from the measurements. The home hub receives the wireless transmission of measurement data, processes the measurement unit data for effecient transfer, and transmits selectively data processed by thereby via public a data transmission network to a health data management unit.

10 Claims, 5 Drawing Sheets

HOME HUB FOR REPORTING PATIENT HEALTH PARAMETERS

FIELD OF THE INVENTION

The present invention is related to techniques for capturing a patient's health parameter data and more particularly related to techniques for capturing patient measurements in a nonclinical environment and reporting the patient measurements to a remote health management center.

BACKGROUND

In many countries, e.g., the United States, the general population is getting older on the average. A phenomenon that occurs with an aging population is more long-term ailments that impair the normal physiological functions of a person. In many cases such chronic health problems are not immediately life-threatening to a patient and the patient may not benefit significantly from hospitalization. However, often it is necessary to monitor the day-to-day health conditions of a patient for clinicians to provide adequate care to such an individual. Management of chronic illnesses poses unprecedented challenges to the existing healthcare structure and the delivery of its services. Heart failure, coronary heart disease, unstable angina, heart rhythm disturbances, hypertension, diabetes, asthma, congestive obstructive pulmonary disease, and depression are examples of ailments that need diligent patient contact and measurements in order to institute timely management of the patient's problems before they develop into an untoward clinical course requiring more intensive and expensive management, including hospitalization. For example, for health maintenance, a patient with a risk or history of congested heart failure may need to monitor regularly his weight, blood pressure, temperature, and blood sugar and report the data to a clinic.

For the reason of convenience, if practicable, it is often preferable for a patient to make health parameter measurements. It is advantageous in allowing patients to perform such measurements and report the data to the clinician. To this end, health monitoring systems need to be developed to provide such measurement and reporting functions. In the past, health monitoring required patients to take these measurements manually and report the results either by telephone or by recording them on paper. The human involvement in this process results in the potential for error in reporting the measurement data. Also, significant effort is required to record and manage the patient data by the clinician. Cost effective, secure and confidential remote connections between patients and their clinicians can help to prevent serious, episodic, expensive clinical courses and provide a better quality of life for remotely managed patients.

Because clinicians rely on the data to diagnose and advise the patients, the system should present the necessary health data information in a easily understandable format. Also, it will be beneficial for the system to be versatile so as to provide patient information to a variety of related professionals. For example, patients that need attention and follow up need to be flagged using limits for each patient previously provided by the patient's clinician. Individual patient review of measurements provided in a unified view may be needed to provide dependable patient management.

Furthermore, the system should be reliable. A system that fails to report data when measurements are taken or fails to receive the transmitted data when the data are communicated from the measurement device will compromise the effectiveness of a program that monitors the health and well-being of the patient.

Although both the clinician and the patient may have the desire to monitor the health parameters of the patient consistently, the patient, being impaired physically, may find it a challenge to perform measurement procedures. Therefore, a system that is complex and requires extensive deftness and multiple steps of manipulation to operate will discourage the patient from complying with a monitoring program prescribed by the clinician. There is a need for a health monitoring system that is easy to use.

Techniques and systems for remote monitoring and reporting have been described in the literature. Examples include U.S. Pat. No. 4,803,625 (Fu et al.); U.S. Pat. No. 5,142,484 (Kaufman et al.); U.S. Pat. No. 5,265,010 (Evans-Paganelli et al.); U.S. Pat. No. 5,331,549 (Crawford); U.S. Pat. No. 5,357,427 (Langen et al.); U.S. Pat. No. 5,404,292 (Hendrickson); U.S. Pat. No. 5,558,638 (Evers et al.); U.S. Pat. No. 5,576,952 (Stutman et al); U.S. Pat. No. 5,626,144 (Tracklind et al.); U.S. Pat. No. 5,704,366 (Tracklind et al.); U.S. Pat. No. 5,732,709 (Tracklind et al.); and U.S. Pat. No. 5,832,448 (Brown). Many systems reported in the literature suffers from the lack of reliability, convenience, and flexibility. For example, some systems may fail to report when a measurement unit fails to function properly. Some systems are cumbersome for the patient to use. Yet some systems do not provide the flexibility of data reporting and administration needed by health care professionals. Thus, there continues to be a need for a remote monitoring and reporting system for monitoring the health parameters of patients. Furthermore, there is a need for a measurement unit for collecting data reliably, as well as a need for a mechanism for managing and transferring the data to a data management center.

SUMMARY

The present invention provides a technique for reporting a patient's health parameters to a remote data management center. In one aspect, an apparatus of the present invention for reporting a patient's health parameter includes one or more measurement units each having sensor(s) for sensing measurements of one or more health parameters. The measurement units each include a transmitter for wirelessly transmitting data derived from the measurements (measurement data). A home hub included in the apparatus receives the wireless transmission of measurement data, processes the measurement unit data for efficient transfer and transmits selectively data processed by the home hub (hub data) via a public data transmission network to a health data management unit. In an embodiment, the measurement unit and the home hub each keep a relative time to associate with measurements such that absolute time-keeping is not needed therein. This obviates the need to frequently adjusting a clock in the measurement unit or the home hub to synchronize with an external clock.

The present invention measures health data from a patient and relays the patient measurement data from a home health care measurement unit (device) to a data storage and management system at a site remote from the patient. The invention includes a device that resides at a place of convenience of the patient. Two data networks can be used for the transmission of the measurement data.

The present invention can be advantageously used for monitoring the health parameters of patients. It provides for simple operation that requires very little effort on the part of the patient. Automated patient measurements reduce the potential for error by minimizing human involvement in the reporting of the data. The present invention also eases the workload of the clinician managing the patient by automating the capture, reporting, and management of the data. In the embodiment in which wireless transmission is used between the measurement units and the home hub, tremendous flexibility is available in placing the home health care device relative to the home hub. Installation of the devices is made easier because there are no wires used to connect the home hub with the measurement units. The use of the public telephone system allows for the use of standard equipment with low cost and easy installation. Further, the data management system of the present invention allows for great flexibility in information management. By using LAN and/or the Internet, individuals with a variety of needs and technical expertise, over a wide geographical area can access the information to obtain the information they need, even to input their own feedback to the data management center (e.g., feedback to the clinicians).

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION

In the present invention, a home health care device is used in a system to capture patient measurements (e.g. weight, electrocardiogram (ECG), pulse, temperature, blood pressure). These measurements are transmitted to a data storage and management system that is at a location outside the home. This allows a clinician at a location outside the home to view the measurement data for the management and assessment of the patient's health.

Figure 1:
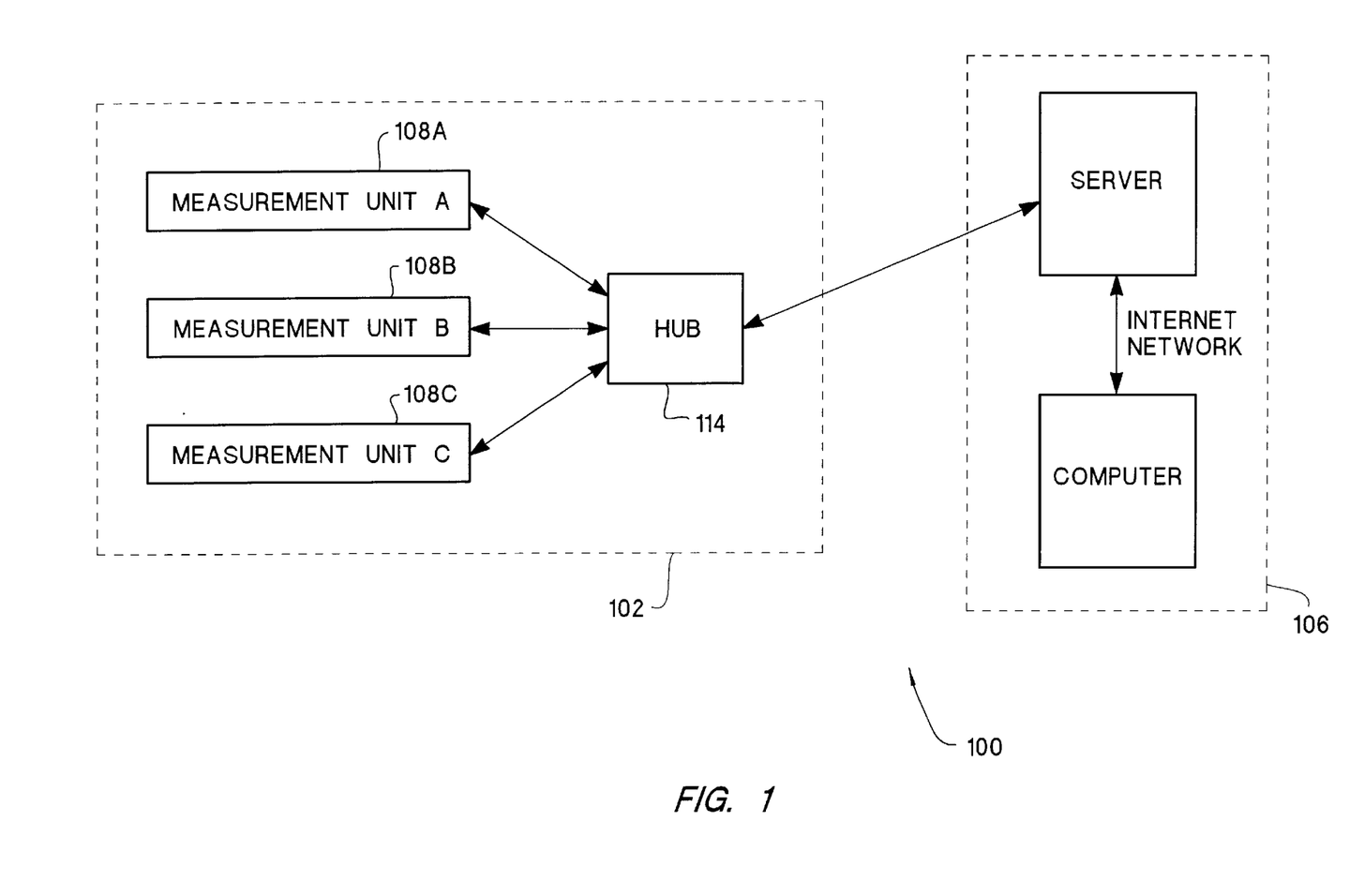
FIG. 1 is a block diagram of an embodiment of the system of the present invention.

FIG. 1 depicts a block diagram showing the structures (hardware) of a system of the present invention that enables the capture of patient health data and reporting to a patient data management center. In general, the system 100 includes hardware items that are located in a nonclinical environment (e.g., the patient's home) 102, in which a patient's health data are taken, and a data management center (e.g., an environment for collecting patient data such as in a hospital) 106 remote from the nonclinical environment 102. The data management center 106 manages the health data to provide access by health-care professionals. Although a person skilled in the art will be able to practice the present invention with the present disclosure, further details of an embodiment of an applicable system for remote patient monitoring is described in copending patent application "System for patient monitoring," invented by Cruse et al., application Ser. No. 09/290,210, filed on the same day as the present application, which is herein incorporated by reference in its entirety. Further details of an embodiment of an applicable data management center is described in copending patent application "Data management center for patient monitoring," invented by Tudor et al., application Ser. No. 09/290,149, filed on the same day as the present application, which is herein incorporated by reference in its entirety.

Measurement Unit

In the nonclinical environment 102, the patient's health parameters are measured by measurement units 108A, 108B, 108C for parameters A, B, and C. As used herein health parameters of a patient are parameters that have bearing on the health condition of the patient and can be measured from the body of the patient (e.g., blood pressure, pulse rate, electrocardiogram (ECG), weight, temperature, blood glucose). It is to be understood that many other parameters can be measured with addition measurement units (hereinafter also referred to as "device" unless "device" is specified to be otherwise in the context) and reported to the data management center 106 if desired. Measurement equipment suitable for measuring standard health parameters are well known in the art. For example, blood pressure measurement can be done with pressure transducers and the electronics for converting the pressure data to electrical signal that can be transmitted. Temperature can be measured by temperature transducers such as thermocouples, thermistors and the like, to provide electrical signals that represent the temperature data. ECG can be measured by electrodes placed on the body surface of the patient. Blood pulses can be sensed by deriving from the blood pressure measurements, by using a sound sensor to sense the sound of the heart or blood flow through restrictions. The weight of the patient can be measured by an electrical scale. Blood glucose can be measured by spectrometrically using chemical reaction and optical analysis. It is understood that appropriate electronics will be used to associate with the sensors and transducers to provide electrical signals for transmission to the home hub and to the data management center 106.

Figure 2:
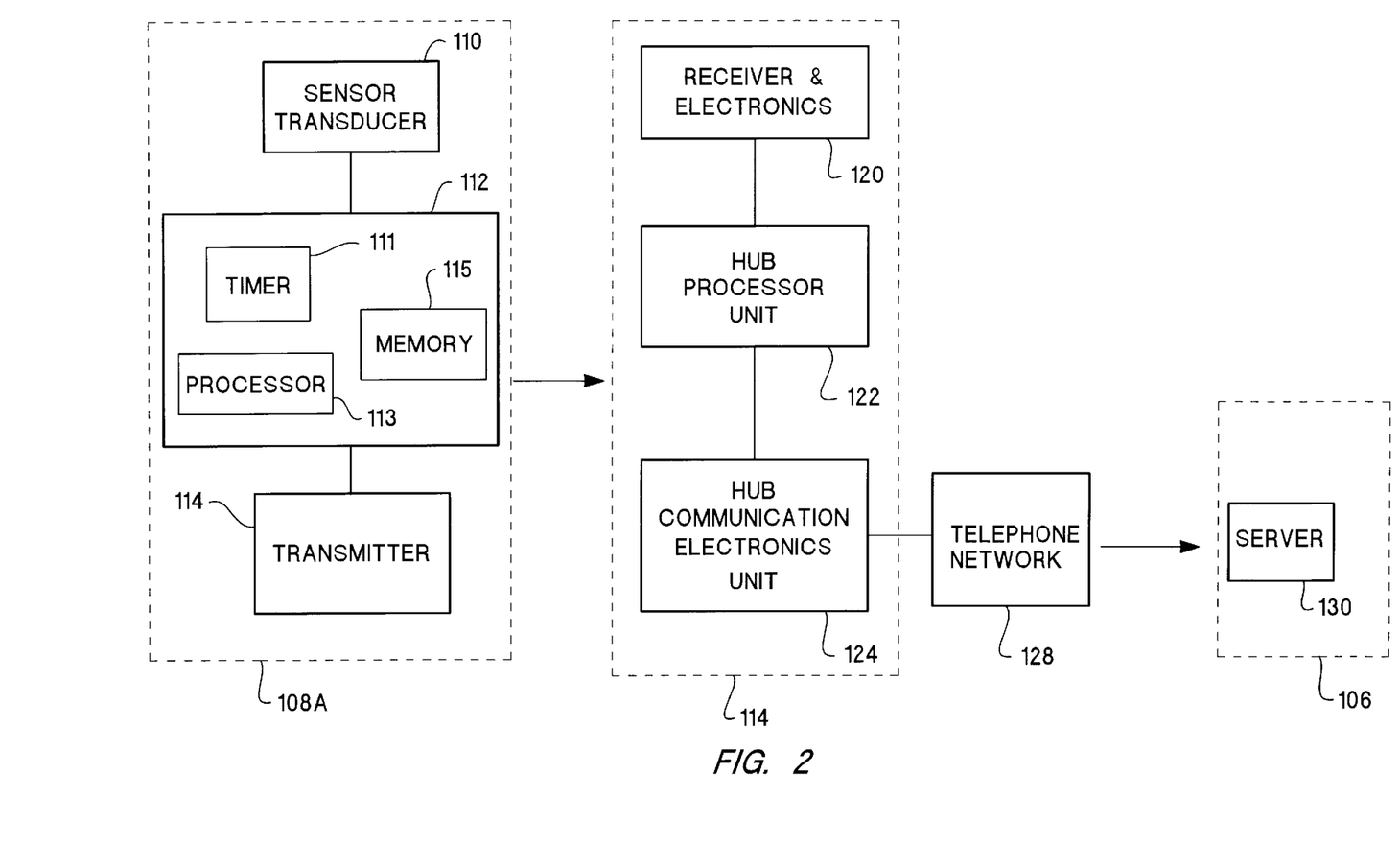
FIG. 2 is a block diagram of an embodiment of the system of the present invention in more detail.

FIG. 2 illustrates a block diagram depicting an example of a measurement unit (e.g., measurement unit 108A). The sensor transducer 110 receives the physical data of the health parameter (such as blood pressure) and produces corresponding electrical signals. The measurement data being transferred from a measurement unit to the home hub have time data associated with them. The time data can be provided by a timer 111 in the measurement unit to provide time stamps corresponding to the measurement data to provide a time basis for the measurement data. Although the timing data can be based on real-time (absolute time), alternatively it can be relative time so that each time stamp corresponds to, for example, 30 seconds of real time. A memory 115 stores the measurement and time data. The corresponding electrical signals are processed by appropriate electronic circuits 112, (which can include a processor 113, and circuits for filtering, amplification, etc.) to be further transmitted by transmitter 114 as wireless signals. In a preferred embodiment, the processed signal is transmitted as radio frequency (RF) signal to a home information control gateway or hub (hereinafter "home hub" or "hub") 114 via a RF link. (The home hub 114 and the data management center 106 will be described later.) Other wireless signals such as microwave, infrared signals can also be used. Techniques and instruments or devices (such as transmitters, receivers, signal processors) for data transmission by such mechanisms are known in the art. In one embodiment the network that allows a home health care device to send patient measurement data to home hub uses RF of 418 MHz. Another uses 900 MHz. Both are carrier-on/carrier-off (OOK, or on-off keying) receivers. It is understood that other similar means and frequencies can be used.

Data Transmission

Measurement generated by the transducer and the time stamps are stored to provide historical data. The historical data are transmitted in episodes of transmission so that at each episode some old data that have been transmitted before are transmitted along with new data that have never been transmitted before. Thus, data transmission is done in a scrolling fashion such that at least some of the historical data are transmitted in multiple transmission episodes. In these transmission episodes old data are replaced with new data in a first in first out manner.

To this end, in an embodiment a measurement unit maintains a 16 bit value which is used to denote relative time, referred to as the unit's "current tick." Each tick unit represents a 15-second interval. (It is understood that other intervals, e.g., 5 second, 30 second, etc., can alternatively be used.) In an embodiment the measurement unit was designed that it can measure elapsed time covering a range of 65,535 ticks=983,025 seconds=16,383 minutes=273 hours=11.4 days.

A measurement unit marks the time for a message item ("Msgitem") (a measurement or status event) with the current tick value, which is referred to as the Msgitem's item tick. At any given time, the item tick can be compared to the measurement unit's current tick value to determine how much time has elapsed since the Msgitem occurred. The elapsed time in seconds is calculated with the following pseudo code: If item tick is less than or equal to (<=) current tick, then Elapsed time in Seconds=(current tick−item tick)×15

Else

Elapsed time in Seconds=(65536−(item tick−current tick))×15.

When a measurement unit sends a message, the current tick value is set in the message header. A receiving device (instrument) can determine the elapsed time of a Msgitem by comparing each item tick to the current tick value in the header. It is assumed that the transmission time from sender to receiver is instantaneous such that the current tick value corresponds to the time of reception.

To increase the probability that data will be transmitted successfully from a measurement unit to the clinical database in the home hub, the measurement unit will transmit data multiple times. Additionally, a measurement unit will keep a history of measurements that will be retransmitted along with the current measurement. An embodiment of an retransmission algorithm is described below. To verify that the data received match the transmitted data, a Cyclical Redundancy Check (CRC) will accompany the header and body of each device message. The CRC algorithm used is the CCITT (ITU-T) algorithm as implemented in "Numerical Recipes in C, 2$^{nd}$ Edition", Cambridge University Press, ISBN 0 521 43108 5, Copyright 1987, 1988, 1992.

Retransmissions of a datum are done at increasing intervals (e.g., 1, 2, 10, 60 minutes). Some randomness is added to the interval to increase the probability that measurement units in the same location do not retransmit at the same time (and thus create collisions). The intent of the pattern is that "more effort" is made early on to get data to the home hub. After an initial effort is made, the interval increases to allow other measurement units room to transmit their data. The home hub keeps a Msgitem history that keeps track of what Msgitems have been received from measurement units. As the home hub receives device messages, duplicate Msgitems are discarded and new Msgitems are added to the history. The home hub only forwards data when new Msgitems are added to its history. This prevents device retransmissions from causing excessive home hub activity. The interval between transmissions is small near the event, and grows to a much longer steady-state interval. It is expected that the actual transmission period for each measurement unit is small with respect to the interval between transmissions and that more effort is made within the first 5 minutes after an event occurs. To this end, the following algorithm can be used:

$T_{delay}$ is the delay between the start of each transmission.

N is the pseudo-random seed between 0 and 1 (i.e. a fraction) N is set at the initial transmission or event.

The content in the brackets indicate the stage of transmission and retranmission.

| | | |
|---|---|---|
| $T_{delay}[0] =$ | 0 (initial transmission occurs at or near the event) | |
| $T_{delay}[1] =$ | (30 + N × 30) second | (mean = 45 second) |
| $T_{delay}[2] =$ | (60 + N × 60) second | (mean = 90 second) |
| $T_{delay}[3] =$ | (600 + N × 600) second | (mean = 15 min) |
| $T_{delay}[4] =$ | (3600 + N × 3600) second | (mean = 90 min) |
| $T_{delay}[\text{steady-state}] =$ | (14400 + N × 14400) second | (mean = 6 hours) |

Thus, one can expect transmissions from one measurement are as follows:

1) transmission occurs immediately following an event (e.g., measurement or reboot)
2) transmission occurs 45 seconds after the first transmission
3) transmission occurs 90 seconds after the second transmission
4) transmission occurs 15 minutes after the third transmission
5) transmission occurs 90 minutes after the fourth transmission
6) subsequent transmissions occur at 6 hour intervals after the fifth transmission.

The cycle restarts after another measurement is taken. If no measurement is taken for 11.4 days and the data expire from the queue, no data are sent but the periodic status items are sent. This gives three transmission attempts within the first 5 minutes while still allowing other measurement units a reasonable opportunity to communicate.

To effect redundant data transmission, each measurement unit keeps a history of the measurements that were taken. The history is needed so that measurement values can be retransmitted. The measurement history should store the measurements with the associated item sequence number (itemSequenceNum) and item tick. The measurement unit only stores its history up to a fixed length. When the history is full, the oldest measurement is deleted before adding a new measurement (FIFO). For example, a measurement unit would remove an item before 11.4 days have elapsed since the measurement was taken. After 11.4 days, the devices current tick value will wrap around.

A measurement unit can transmit information about a variety of characteristics of the measurement unit to the home hub. The measurement units can contain a resident self-test and the results of this self-test will be communicated over the RF link and through the home hub to the data management center 106. Battery operated units will check their battery status and communicate a weak battery to the data management center 106. Before the measurement units stop functioning, they will tell the patient and indicate to the clinician that batteries need replacement. When first started, the measurement units can be made to flash a LED when batteries are low. As examples, the characteristics (item type) can include the following:

DeviceReboot

When a measurement unit is first turned on or re-boots, it will send a DeviceReboot item to the home hub. This item is forwarded by the home hub and indicates that the measurement unit has powered on.

DevicePing

A measurement unit will be able to transmit a DevicePing item to the home hub. This item will not be forwarded by the home hub, but will simply indicate that the measurement unit is present. The home hub can provide an audible tone as feedback to the user on receipt of this item. The DevicePing item is designed to assure the user that measurement unit is within range of the home hub. It is usually sent in a message along with other static data (manufacturer, model, serial number, etc.) to ensure that this information reaches the home hub and to show that a reasonably sized message can be transmitted.

DeviceStatusGeneric

All measurement units will report a limited amount of status information that is common to all measurement units. This will include information on the number of measurements sent by a measurement unit, the number of measurements aborted, and transient flags for battery-warning, no device activity, and hardware malfunction. This DeviceStatusGeneric item is sent along with any measurement data and at reboot. A change in status does not (in and of itself) trigger a transmission. A measurement unit can keep a 16-bit count of the number of measurements taken since reboot. This counter should wrap around. If such a term is meaningful to the measurement unit, it should keep a count of the number of aborted measurements. This is a generic counter of all aborted measurements. A measurement unit used on a daily basis will set a DeviceNoActivity flag if a patient has not used the measurement unit for 36 hours. This item is a way to indicate use by a patient and also ensures that the measurement unit sends a message to the home hub even if the measurement unit is not used. This flag is reset when a measurement is taken. Measurement units (i.e., devices) that have a way of detecting battery level should set the DeviceBatteryWarning flag so that the clinician can be alerted that the batteries need to be changed in the measurement unit. Units that detect a hardware malfunction but are still capable of transmitting data should set the DeviceHardwareMalfunction flag and send a status message. This message item may be augmented by a device-specific status message item. This is intended to be a generic way of alerting the system that an error has occurred.

DeviceSerialNumber

Data on the serial number of the measurement unit is transmitted to the home hub when the measurement unit sends its "static data."

DeviceFirmwareRevision

The measurement unit also reports a firmware revision.

DeviceRfTest

A measurement unit can also transmit an item designed to help diagnose and characterize the RF transmission from a measurement unit. This will contain a specified data packet that can be analyzed by the home hub. All measurement units will send the same DeviceRfTestMessage. The DeviceRfTest message item is designed to take a substantial amount of time to transmit and is intended to catch RF interference which can then be analyzed. For example, this message can simply contain all binary byte codes from 0 to 255. This predictable byte stream can be parsed by the home hub to determine an analog to bit error rate.

DeviceBatteryLevel

For measurement units that can measure the actual battery level, it should be reported. To have a reference point, the expected full scale voltage is reported along with the current battery voltage.

DeviceManufacturer

A measurement unit also reports its manufacturer name as an ASCII string. This data should be transmitted to the home hub along with all other static data.

DeviceModel

A measurement unit also reports its model name or number as an ASCII string. This data should be transmitted to the home hub along with all other static data.

DeviceCapabilities

A measurement unit also reports the measurement-related item types supported by the unit. These data are transmitted to the home hub along with all other static data.

DeviceHardwareRevision

If a measurement unit supports the detection of a hardware revision, a hardware revision is also reported.

DeviceDebug

This item is present to allow measurement unit to send data through the home hub during firmware development. This type is reserved for the measurement unit debug purposes.

Figure 4:
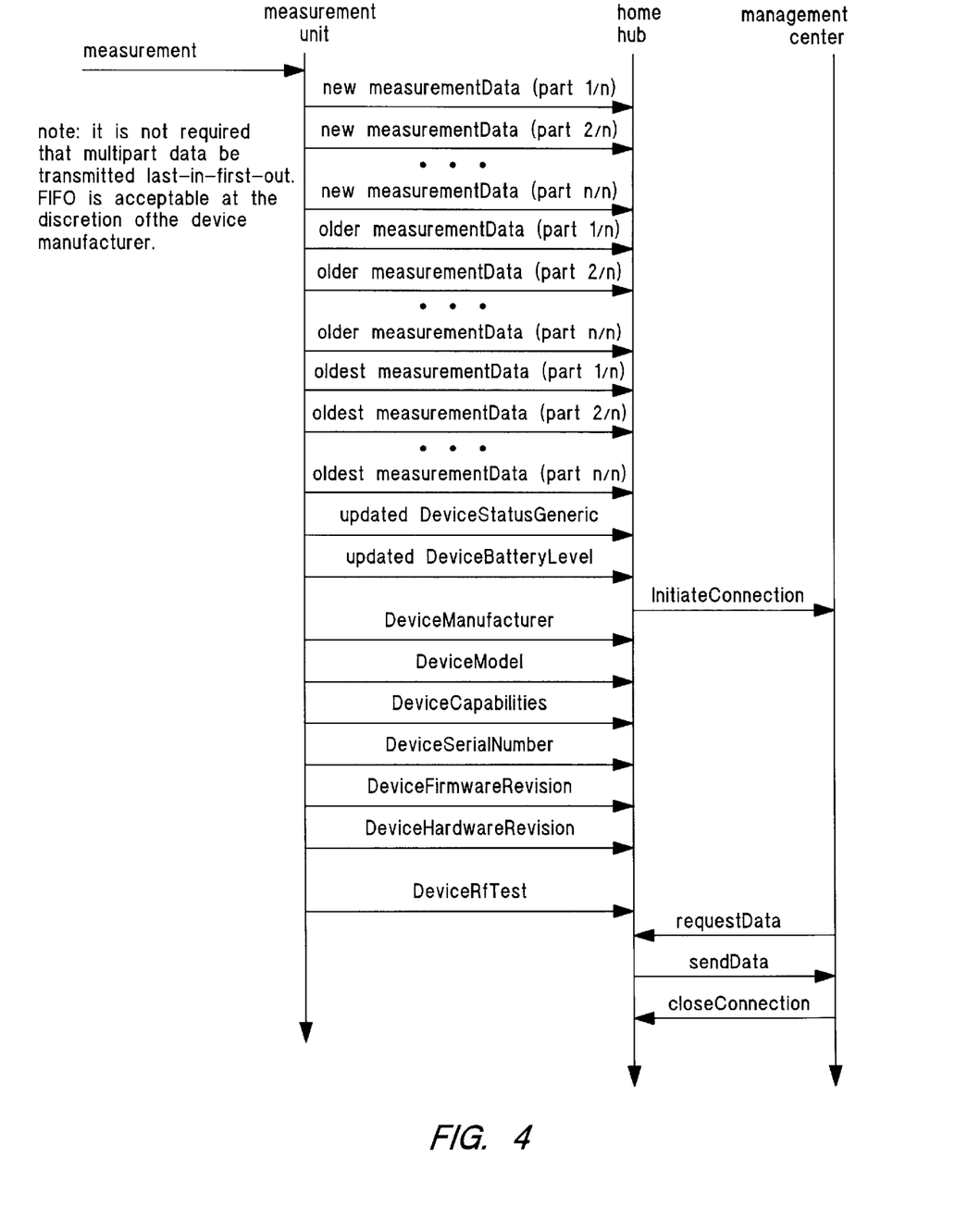
FIG. 4 is an illustration showing the transmission events from a measurement unit to the home hub to the management unit in an embodiment of the present invention.

The occurance of one of the following events would trigger a transmission (or set of transmissions) by a measurement unit to the hub: reboot/self-test, "TestButton" pressed, measurement taken, retransmission delay expires, and no-activity interval expires. If appropriate, the measurement unit should also transmit information if a hardware or software error occurs. FIG. 4 shows an illustration of the transmission events from a measurement unit to the home hub to the management unit. It is noted that a measurement unit takes measurements of health parameters from the body of the user and transmits the historical data of these measurements as well as information on the measurement unit status to the home hub. The historical data include the new measurement data (shown in FIG. 4 as including parts 1/n to n/n where n are data numbers in the new measurement). The historical data also include older measurement data and oldest data (relative to the other transmitted data in the particular episode of transmission). Further, the measrement unit also transmits the updated DeviceStatusGeneric and the updated Device BatteryLevel. The DeviceManufacturer, DeviceModel,DeviceCapabilities, DeviceSerialNumber, DevicefirmwareRevision, and DevoceHardwareRevision are transmitted when the measurement unit transmits the "static data," which are standard nonmeasured data that are sent with each set of measurement messages. This redundant transmission ensures that the information needed for downstream measurement unit discovery will be received in a timely manner.

Ease of Use

Measurement units are designed to be simple for the patient to use. In more detail regarding an embodiment, all of the measurement units 108A, 108B, 108C, etc., have a common "display and control" panel with an easy to read label identifying what they are, e.g. "Weight." Indicators and controls on the measurement units are the same wherever possible. For example, the scale requires only that the patient stands on the scale for a few seconds and step off. The scale zeros automatically and transmits the weight without other interaction from the patient. The blood pressure unit (i.e., the measurement unit that measures blood pressure) requires the patient to slide a blood pressure cuff onto his/her upper arm and then press a "Start Button." The blood pressure unit in addition to measuring pressures can also measure pulse rate. A rhythm strip unit requires that the patient to put on "watch band" wrist electrodes or place adhesive electrodes where instructed by the clinician, and then press the Start Button. The measurement units can be made such that they will prompt the patient when the measurement is complete by sound and/or visual indication.

The measurement units 108A, 108B, 108C, etc., are placed at various locations within the nonclinical environment, e.g., home, as needed. They are designed to use little power and can be operated using line electricity or batteries. For battery-operated units, since they do not need to have any external connections including power cords, they can be located in the home where it is convenient. Furthermore, the measurement units can be designed to be resistant to liquid spills. Although measurement units can be made to make frequent measurements and accommodate a fast data transfer rate, generally for health parameters the units will function adequately with low data rates and infrequent measurements.

As an example of a measurement unit, a scale is used to measure the patient's weight. Other measurement units can be used for measuring blood pressure, cardiac rhythm, body temperature, and the like. See copending application Ser. No. 09/290,210, "Patient monitoring and management system," which is incorporated by reference herein. Preferably, the scale is made such that most of the functions are automatic. The patient can simply stand on the scale and the scale will turn on automatically and prompt the patient to stand still. After the patient's weight is measured, the patient is prompted to step off. Prompts can be provided by sound (voice) and LED indicator. The weight is indicated on the display on the scale, announced by voice and is automatically reported to the home hub and then to the data management center (which can be done over the patient's regular telephone line). The measurement unit can be made such that the only user control is the volume button, which adjusts the loudness of the voice. Volume level is indicated by spoken sound at each push of the button. A grab bar is supplied with each scale and can be attached to the scale's platform to help stabilize unsteady patients and to bring the sound and display closer to the patient. The weight the patient applies to the grab bar is also weighed by the scale and is included in the total patient weight reported. The weight of the grab bar itself is not included in the patient's reported weight. The scale in its zeroing step takes into account of the weight of the grab bar to render a "zero" reading before a user steps on the scale. The display unit associated with the scale for reading the weight can be mounted on the scale itself, mounted on a post that is connected to the grab bar, or be a part of the grab bar. For more accurate performance, the scale should be placed on a level, hard floor.

Home Hub

The home hub 114 receives data transmissions from the measurement units, which can include a single unit or many units for reporting a variety of parameters. Measurements are reported by the home hub 114 to the data management center 106 using a telephone network, such as the public telephone system ("PTS"). Of course, dedicated telephone systems can be used if desired. FIG. 2 shows in block diagram that the home hub 114 includes a receiver (including an antenna) 120 and its associated electronic circuitry for receiving the wireless electromagnetic signal (e.g., RF signal) from the measurement unit(s) (e.g., units 108A, 108B, etc.). For example, the circuitry can include an RF module that takes the RF signals from the antenna and converts the signals into a serial byte stream.

Asociated with the home hub 114 are electronics and equipment used for the processing of information, directing communication, processing information through the PTS, and the like . Such electronics and equipment will be clear to one skilled in the art. For example, the home hub 114 will have processor(s) used for doing calculation, communication, and controlling other equipment. Further, there are memory units (which can include RAM, ROM, hard drives, CD drives, backup tape drives, floppy drives, etc., with their respective storage medium) for storage of programs, algorithms, and data. The programs, algorithms, and data stored in the memory units would be structured according to programing techniques, databases and data structures for effective input, execution of processes and retrieval of information. Such techniques and structures for programing, data managing and processing are known to those skilled in the art.

In an embodiment of a home hub 114, a hub processor unit 122 is electronically connected to the receiver and associated electronics 120 for managing the measurement data to report to the data management center 106 by the hub communication unit 124 (including corresponding electronics). The hub communication unit 124 transmits the information (including data), as directed by the hub processor unit 122, through the telephone network 128, to the data management center 106.The data management center 106 includes a computer (server) 130 which manages and controls the flow of the measurement data information it receives from the hub 114. In addition to direct dial-in access through the public telephone network, other alternatives for the communication from the home hub 124 to the data management center 106 are practicable. Instead of a point to npoint telephone call, it is also possible to use the Internet for transferring the patient data. This can also make use of telephone networks. The home hub 124 would perform a dial-in to an Internet Service Provider (ISP) such as America On Line, CompuServe, and the like, rather than directly to the server at the data management center 106. At this point, one alternative would be to create a network connection, through the Internet, with the data management center 106. Another alternative is to send an email message containing the patient data through the ISP to the data management center. With either choice, encryption of patient data may be desired. These solutions differ in cost, security (interaction with firewalls and the need for encryption), and reliability of data transfer. Techniques for such direct-dial data transmission by telephone line or via an ISP from one computer to another are known in the art. Also, alternate methods of sending data from a measurement unit via the Internet to the data management center can be used. For example, one method uses a universally accessible healthcare device having a communication path and a server, wherein the healthcare device generates a set of medical information and the server provides access to the medical information using an open standard network protocol on the communication path. HTML Files may be generated on the fly by the server in the measurement unit See, e.g., U.S. Pat. No. 5,857,967 (Marcos Frid et al.), which is incorporated by reference in its entirety herein.

The features and functions of an embodiment of an applicable home hub and an embodiment of an applicable data management center are described below. Although the home hub 114 can transmit data associated with absolute time to the data management, the home hub, like the measurement units, can use relative time by means of time stamps (current tick), see above. The home hub 114 can have a timer for providing relative time on events at the home hub. Memory in the home hub 114 provides for storage of data, programs and algorithms, and the like.

In one embodiment, the home hub 114 does not edit the measurement data but simply forwards it via a call to the data management center 106. The hub has a device address, which can be preprogrammed (e.g., when the measurement unit is made in the factory) such that the home hub can be identified by the data management center 106 among many home hubs that may be connected to the same data management center 106. The factory preprogrammed device address of the home hub is reported whenever a call is made. Although home-hub can be made to enable two-way communication with the data management center, if desired, the home hub can be made to only originates calls and not answer calls by the data management center.

The processor unit 122 is programmed to control the information transmission in the following manner. Since the home hub shares the patient's telephone line, it gives the patient priority use of telephone by freeing the telephone line whenever it detects a receiver is lifted or waiting to make a call if the patient is already using the line. Immediately after any new measurement is reported to it by a measurement unit (e.g., unit 108A), the home hub dials the data management center 106 if the patient's telephone is not in use. If the telephone is in use immediately after new measurements are made, the home hub waits until the line is free before initiating the call to the data management center 106. Preferably, the measurement unit is made to operate with adequate speed that a call generally last less than one minute. The home hub call is terminated if the patient picks up the receiver (the telephone becomes "off hook", for example, when the patient wants to make a telephone call). In this case, to make a call, the patient would hang up the telephone for a second or two and then pick up the receiver again to get a dial tone. If there have been no new messages received by the home hub in the last approximately 24 hours, the home hub makes a call to the data management center 106 anyway. This tells the data management center 106 that the home hub is still in telephone communication and that the home hub has not received data recently. If the power goes down and back up, the home hub will call the data management center 106 in a few minutes after power is turned on. If a call is unsuccessful for any reason (e.g., when the data management center is busy or for any reason does not answer) the home hub retries periodically until it is successful in connecting to the data management center.

The home hub will send a given message to the data management center once. After the home hub sends the message items (e.g., in response to a request for a new message from the management center server), the management center server will send a "clear messages" request message which indicates that the measurement unit messages have been successfully received. However, due to the redundancies built into the measurement unit communication protocols it is possible for the home hub to send a given message more than once. To discard duplicate messages. Each measurement unit message has a key that uniquely identifies itself. The management center server discards any measurement unit message that it receives which has the same key as another measurement unit message received. In an embodiment in which the current tick wraps around after about 12 days, the management center server should also only consider messages received 65535 ticks (about 11.4 days) prior to the received message when searching for duplicate messages. This is because the measurement unit message's current tick is part of the key and the tick value if allowed to wrap around which could result in measurement unit messages older than 65535 ticks having the same key as a newly received measurement unit message (where both message are distinctly different).

The home hub is made such that it has the standard connecting features that allow for easy connection to the patient's telephone line at any convenient telephone outlet. A modem permits the transfer of information from the home hub to a computer at the data management center 106 via the telephone line. If telephone equipment (e.g., telephone) is already connected, the home hub can be connected directly to the outlet and other telephone device(s) daisy chained to the home hub's extra RJ11 connector.

Preferably, the home hub is small to allow it to be mounted flat beside or under the telephone. It attaches to a nearby power outlet using a power module and to a modular telephone connection. The home hub preferably contains LED indicators (displays) to indicate the state of message transmission to facilitate installation and troubleshooting. For example, a green LED can show that the home hub has received data and that it is waiting to be transferred over the telephone to a server in the data management center 106 and a yellow LED shows that the home hub is using the telephone line to call the server. A button can be placed on the home hub to aid an installer by manually causing the home hub to make a connection to the server.

Error checking of electromagnetic wave (e.g., RF) and telephone messages ensures that valid data is communicated to the data management center 106. Along with this data, information about the state of the measurement units is also communicated, such as battery condition and the reliability of RF communications. The home hub and the measurement units check communication links even when no measurements have been recently made. This tells the clinician that the communication links are functional and that the lack of recent measurements is due to other causes.

The hub processor unit 122 in the home hub runs software that controls all of the measurement unit components. The hub processor unit 122 contains the standard components for a computer, e.g., ROM that holds the processor CPU software, RAM that provides memory used by the software, EEPROM that holds any configuration information, and the like. The hub software running on the CPU performs the major communication functions such as: read measurement unit messages received by the RF module, save measurement data, and communicate measurements data to the data management center. In typical operation, measurement data, formatted according to a predefined protocol understood by the measurement unit software, is received via the antenna and RF receiver. The measurement data are then stored in the in RAM and finally communicated over the modem to a remote data storage and management system. As data are received by the measurement unit, they are analyzed by the software to determine if a particular datum has been previously received. In an embodiment, information about the source of the data and time the data were acquired are used to determine if a datum is new or if it has been redundantly transmitted by another measurement unit. If the datum is new, it is stored in a queue in RAM, otherwise it is discarded to reduce the workload of the measurement unit.

Measurement data are stored in RAM until they are successfully transmitted to the remote system.

In use, after new data are stored in the queue, a telephone call is initiated by the home hub to the data management center 106, which contains a remote data storage and data management system. If the call is successful, data are transmitted via the modem in the home hub to the remote management unit. In an embodiment the FTP (File Transfer Protocol) is used for communication. In another embodiment a UNIX "sockets" interface can be used to allow for two-way communication between the measurement unit and the remote system. Once the data have been successfully transmitted to the remote data management unit, they are removed from the measurement unit data queue. Identifying information about the data (source and time of measurement) are kept so that duplicate transmissions can be prevented.

Home Hub Communication With the Data Management Center

The home hub communicates with the data management center via a telephone line. As previously stated, like the the measurement units, it uses relative time by means of time stamps (current tick), see above. It is not necessary that each current tick in the home hub is the same interval as in the measurement unit, as long as the time interval per current tick for each measurement unit and each hub are known to the data management unit. With this knowledge, the data management center can determine the absolute time at which each event occurs in each measurement unit and each home hub. When a measurement unit obtains a datum it marks the current tick. Also, it marks the current tick when it sends data to the home hub. The home hub marks its current tick when it receives data from a measurement unit and it also marks its current tick when it sends a message to the data management center. Thus, the data management center, by tracing back from the time of reception of a message from the home hub based on the current ticks, the data management center will know exactly what happens when at both the home hub and the measurement unit regarding an envent. This technique obviates the need of a real time clock at both the home hubs and the measurement units. It is often troublesome to maintain real time clocks and keep them aligned between different pieces of equipment. Not requiring real time clocks in the measurement units or the home hubs provides a great advantage to the present invention. The absense of a real time clock will render the structures of the measurement units and the home hubs less complex. Further, in one way communication embodiments from a measurement unit through a home hub to a data management center, there is no simple way to update a real time (absolute time) clock in the measurement unit or home hub by the data management center.

Before a home hub can send data, it must connect to the management center's server (hereinafter "server" refers to the management center's server unless specific otherwise in context) using dial-up networking. It first dials the telephone number that connects to the server's modem. It then logs on to, for example, the Microsoft NT Remote Access Service (NT RAS) to obtain network access to the server. Instead of NT RAS, it is noted that other network access services can be used. At this point, the home hub can send data to a socket that is provided by the application software. Once the Home Hub has connected to a server, it will then connect to a TCP/IP (Transmission Control Protocol/Internet Protocol, which is a system software that handles messages such as dividing into packets, adding information, etc.) socket. This socket interface is served by the application software on the server and is bound to an appropriate IP address. Once connected to the server socket, the home hub will wait for request messages from the server, as briefly illustrated in FIG. 4. The home hub sends data to the server by responding to server requests. The server can also send a command to download information into the home hub. The following are examples of requested may be sent by the server to be acted on by the home hub:

(1) Identification, on which the home hub will identify its version of protocol, login name and management unit identification;

(2) Statistics, on which the home hub will provide a variety of statistics such as the number of RF messages received by the home hub, the number of errors, the number of missed messages, the number of times the hub's modem received a busy signal, the number of reboots, etc.;

(3) Configuration, on which the home hub will provide its current configurtation data;

(4) New Configuration, to request the home hub to modify certain configuration parameters, on which the home hub will acknowledge and update data;

(5) New messages, on which the home hub will send all new message items;

(6) Clear messages, which was sent to the home hub to indicate that that the hub's new messages have been received, upon which the home hub will acknowledge;

(7) Close, requesting the connection be closed, on which the hub will end the communication.

Figure 5:
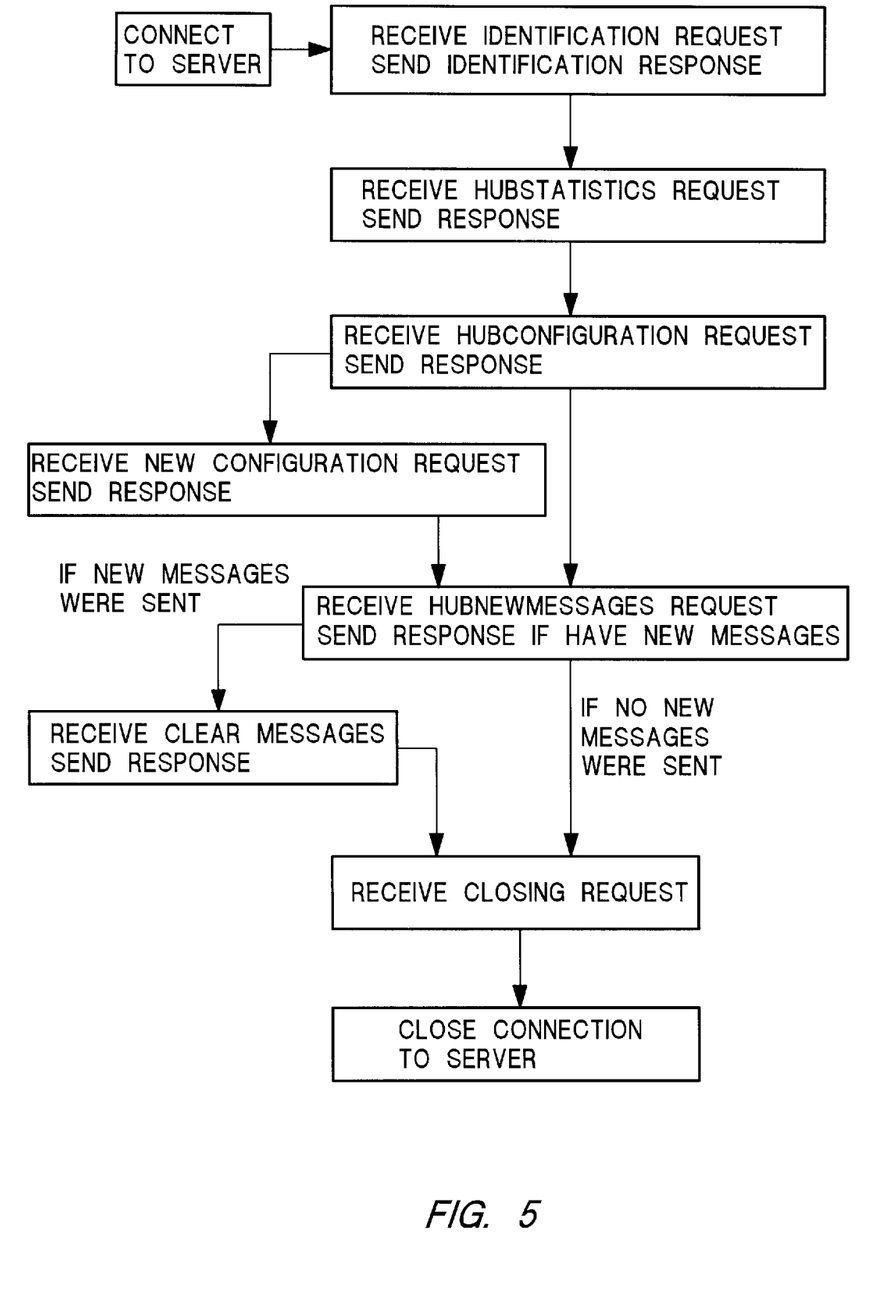
FIG. 5 shows a flow chart illustrating the requests by the management unit and responses of the home hub in an embodiment of the present invention.

FIG. 5 shows a flow chart illustrating the requests by the reserver and responses of the home hub in an embodiment that includes the above requests.

Data Management Center

As already mentioned, telephone lines 128, e.g., the normal (PTS) telephone line can be used to make the connection from the home to a computer (e.g., a server for networking) 130 in the data management center 106. The same telephone line that is already installed in the patient's home can be used. The connection by the home hub 114 to the data management center 106 occurs every time a new measurement is received from a measurement unit. Under certain circumstances, the home hub will also dial the data management center 106 to provide unit status information.

Figure 3:
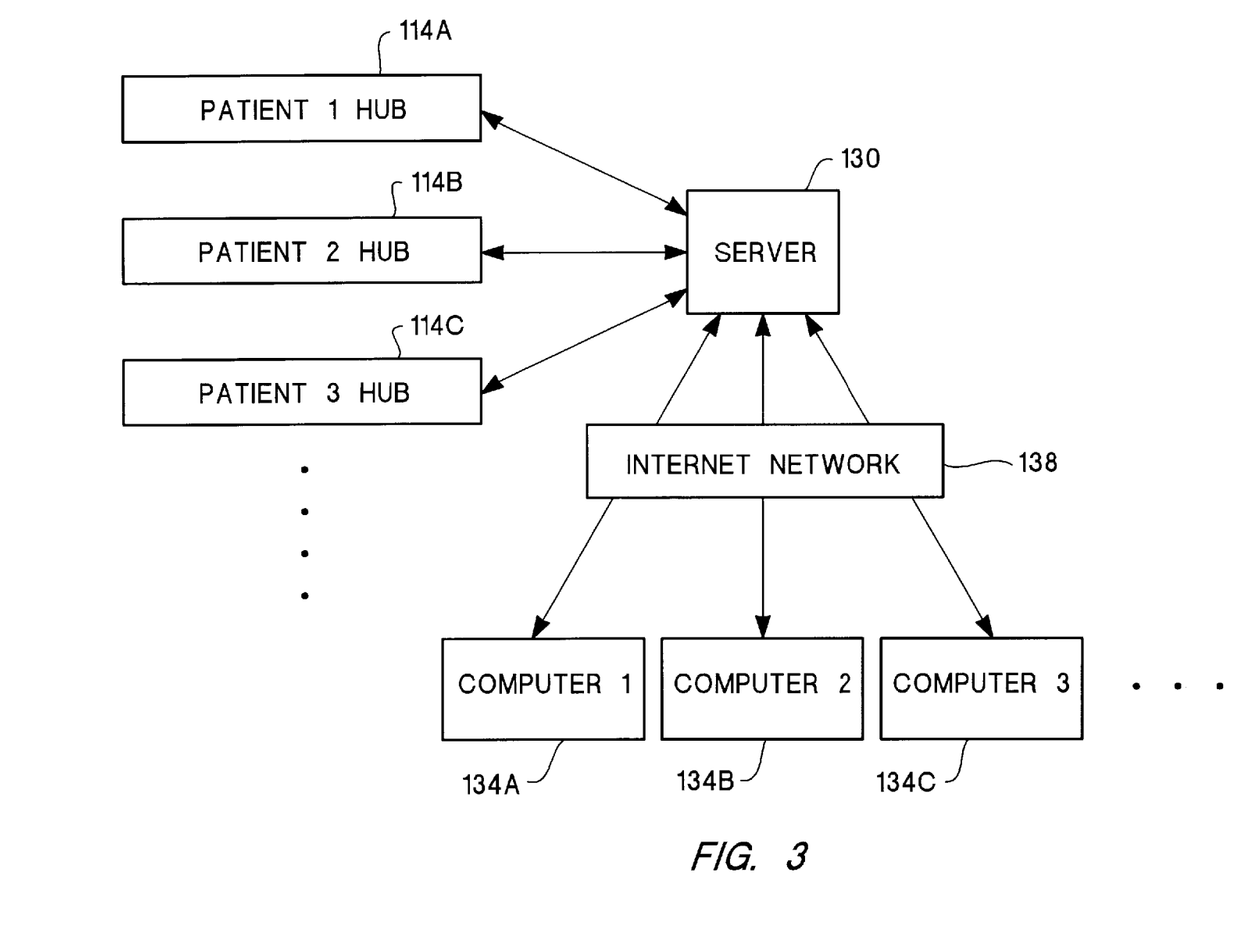
FIG. 3 is a block diagram of an embodiment of the system of the present invention showing multiple home hubs.

It is understood that many patients, and therefore more than one home hub, can be connected to the data management center 106. As shown in FIG. 3, the computer (server) 130 in the data management center 106 is capable of managing communication with many home hubs 114A, 114B, 114C, etc. In an embodiment, one telephone line is used for each of 25 patients. Termination points should be within the proximity of the server 130. These telephone lines are dedicated to home hub communications. Preferably, a single incoming toll free telephone number is used. Local or long distance numbers can also be used. The lines are configured so that multiple home hubs can call at the same time dialing the same number. Each line is connected to a modem port installed on the server. After the server software is installed the new telephone number is entered into the server's configuration. Upon installation, each new home hub will obtain this number from the server 130.

The server 130 (i.e., computer in the data management center 106, which for example can be a minicomputer such as those made by SunMicrosystem Company or Hewlett Company, or a personal computer, PC) is assigned an Internet Protocol IP configuration by the network administrator in order to connect to the LAN (Local Area Network) and the Internet. The server 130 can have its own interface (such as keyboard, pointer, display, sound, printer, etc.) for directly interfacing with an operator. The server 130 also is set up for communicating with a plurality of computers (e.g., personal computers (PCs) such as those made by IBM Company, Compaq Company, Hewlett Packard Co., and the like, which for example may have PENTIUM processors made by Intel Company, minicomputers, and the like) 134A, 134B, 134C, etc., by networking, preferably via the Internet 138 and/or LAN.

To this end, the server 130 has the necessary software and hardware components that enable such functions, e.g., server edition of MICROSOFT WINDOW NT 4.0, RAS card, backup software, firewall security software, scheduling software, utilities, etc. Further, patient management software, such as those providing tracing of health parameters, simultaneous display of multiple patients and parameters, querying, logging, and the like, are also used. It is to be understood that the above examples of functions, software and hardware are given for illustrative purposes and that commercially available or proprietary alternatives can be used. The PC server can also function as part of the "intranet" system for the clinicians. Services can provide dial-in remote support and administration, subject to the customer's security policies, by means of the RAS card.

Clinical application software that can be used in the hub-management center system in includes a clinical client application, which runs on a user's computer (e.g., a nurse station or a patient's PC), and a clinical server application that runs on the server computer, which can also be a PC. The clinical client application is accessible and centrally distributed from the server for quick, non-disruptive installation. The clinical client application is run in the context of an industry standard web-browser, such as NETSCAPE by Netscape Corporation and INTERNET EXPLORER by Microsoft Corporation. Standard Internet protocols, e.g., TCP/IP networking protocol, can be used for communication through the Internet. An industry standard SQL (structured query language) database can be used to run on the server 130. It collects information from home hubs 114A, 114B, 114C, and serves information to clinical client applications. In an embodiment, with appropriate disk and telecommunication facilities, the server 130 stores a year's worth of measurements per patient and supports at least one hundred patients.

The server 130 provides the data for client computers 134A, 134B, 134C for various functions. For example, one computer, e.g., computer 134A, can be operated by a clinician to monitor the day-to-day functions (even moment-to-moment functions, depending on the need) of one or more patient. The typical user is a nurse or a doctor, and is not a computer expert. The application does not require advanced computer knowledge to configure or use. A user may be allowed view or edit capability. The clinical user may be configured to see either all of the patients, or only their own patients. Accessing the data management center via the LAN and/or Internet makes the information easily available practically from anywhere in the world.

A different client computer (e.g., computer 134B) can be operated by a hospital administer to manage the insurance and clinical records. Yet another client computer may be used by the patient, or her family member, to check on the progress of the health status of the patient. To this end, the clinical application includes two modules: review and administration. The clinical review module is the primary user interface. It provides patient health-related data management (such as listing) on individual basis as well as in a group by storing and displaying data on vital signs, self-assessment notes, demographic data, and the like. The clinical administration module is used to manage the general information of patients, such as clinician list, unit list, insurance plan list, and general organizational information and to provide status and diagnostic information for home units and clinical application software. Whereas the clinical review module is used for day to day management of patients, the administration module is meant to handle less frequent changes and updates.

The daily patient review and management will normally be performed from a LAN connected client PC. Oftentimes, a patient will experience symptoms after normal working hours, so the database should also be available via dial-in. The customer's IT department can provide dial-in capability with remote LAN access (using token based authentication and the like) or they can build a VPN (Virtual Private Network, a network of computing and storage elements, their interconnects and routers, where some of the components are part of a public network, which means some part of the VPN nework is not under local administrative control) with private routers or by using encrypted tunneling over the Internet.

Additional Features

Although the embodiment described above utilizes a one-way radio link, provision for a two-way RF link to measurement sources would support additional capabilities as well as more advanced communications protocols. Providing a reverse channel from the measurement unit described here to measurement sources would allow acknowledgment of received messages and reduce the amount of redundant information transmitted by a measurement source. A two-way link can also be used to allow information and program information to flow from the data management center to a home hub, or even to a measurement unit. As an example, a target value (e.g. weight) could be downloaded into a scale. The scale could then inform the user of their weight relative to their target weight. Another use of a two-way protocol would be to download new software or firmware into a measurement unit. Data transmission between the measurement units 108A, 108B, etc., and the home hub 114 can use a simple OOK (on-off keying) RF transmission protocol. It the carrier frequency is on, this is a binary "1," if the carrier is off, it is interpreted as a binary "0." Timing is handled by an industry standard UART (Universal Asynchronous Receiver/Transmitter). The use of spread-spectrum RF technologies, e.g. FSK (frequency-shift keying) allows for higher data rates and more reliable transmission. Also, it increases the security of information transmitted by a source measurement unit.

Although the preferred embodiment of the present invention has been described and illustrated in detail, it is to be understood that a person skilled in the art can make modifications within the scope of the invention, especially in numerical values relating to size, shapes, frequencies, and the like. It is also understood that given the functionality descriptions presented in this disclosure, a person skilled in the art will be able to construct computer programs and algorithms to control equipment and communicate information in accordance with the functionality described herein.

What is claimed is:

1. A method for reporting a patient's health parameter, comprising:

(a) collecting measurements of one or more health parameters;

(b) deriving measurement data from the measurements and wirelessly transmitting the measurement data in transmission episodes of less than about one minute to a processing hub proximate the patient for processing the data; and (c) at the processing hub (hub) processing the data and selectively transmitting data processed by the hub (hub data) in episodes of transmission of less than about one minute via commercial data transmission network to a health data management unit, which is distal the patient and can process the hub data for patient management.

2. A method according to claim 1, further comprising providing time stamps to associate with the measurement data and transmitting the time stamps with the associated measurement data.

3. A method according to claim 2, further comprising providing time stamps to associate with the measurement data and providing time stamps to associate with the transmission from the hub to identify the time of measurement data relative to the time of transmission from the hub to the health data management unit.

4. A method according to claim 2, further comprising storing the time stamps with the associated measurement data in a memory as historical data and transmitting a portion of the historical data in transmission episodes to the hub.

5. A method according to claim 4, further comprising transmitting the measurement data and time stamps in the transmission episodes such that measurement data are replaced in a first in first out manner as new measurement data are derived from measurements.

6. A method according to claim 4, further comprising transmitting the measurement data wirelessly via radio frequency (RF) transmission to the hub.

7. A method according to claim 4, further comprising receiving the transmission of the transmission episodes and identifying duplicated measurement in the hub such that duplicate data are not transmitted to the health data management unit.

8. A method according to claim 4, further comprising storing all or part of the data received from the wireless transmission until at least all new data have been transmitted to the health data management unit.

9. A method according to claim 4, further comprising determining the presence of abnormality in measurement data transmission based on the consistency of the measurement data transmission and transmitting signal to the health management to alert about abnormalities of measurement data transmission received from the wireless transmission.

10. A method according to claim 4, wherein the hub is located in a building and for transmission of hub connected to a telephone link servicing a telephone in the building, the method further comprising interrupting the transmission of hub data to the health data management unit to yield priority to the use of a telephone in the building.

* * * * *